(12) United States Patent
Pryor et al.

(10) Patent No.: US 11,031,115 B1
(45) Date of Patent: *Jun. 8, 2021

(54) PHOTOTHERAPY APPARATUS WITH INTERACTIVE USER INTERFACE

(71) Applicant: LiteCure LLC, New Castle, DE (US)

(72) Inventors: Brian Pryor, Newark, DE (US); Sean Xiaolu Wang, Wilmington, DE (US)

(73) Assignee: LiteCure LLC, New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/571,768

(22) Filed: Sep. 16, 2019

Related U.S. Application Data

(63) Continuation of application No. 16/148,791, filed on Oct. 1, 2018, now Pat. No. 10,413,746, which is a continuation of application No. 15/707,723, filed on Sep. 18, 2017, now Pat. No. 10,086,211, which is a continuation of application No. 15/344,025, filed on Nov. 4, 2016, now Pat. No. 9,764,155, which is a continuation of application No. 14/976,877, filed on Dec. 21, 2015, now Pat. No. 9,498,640, which is a continuation of application No. 14/226,138, filed on Mar. 26, 2014, now Pat. No. 9,216,300, which is a continuation of application No. 12/964,774, filed on Dec. 10, 2010, now abandoned.

(60) Provisional application No. 61/285,762, filed on Dec. 11, 2009.

(51) Int. Cl.
*G16H 20/40* (2018.01)
*A61N 5/06* (2006.01)
*G16H 40/63* (2018.01)
*G16H 40/20* (2018.01)
*G16H 30/20* (2018.01)

(52) U.S. Cl.
CPC ............... *G16H 20/40* (2018.01); *A61N 5/06* (2013.01); *G16H 40/20* (2018.01); *G16H 40/63* (2018.01); *A61N 5/0601* (2013.01); *A61N 2005/0626* (2013.01); *G16H 30/20* (2018.01)

(58) Field of Classification Search
CPC ... A61N 5/06; A61N 2005/0626; G16H 20/40
USPC ..................................... 606/1–15; 607/88–95
See application file for complete search history.

(56) References Cited

U.S. PATENT DOCUMENTS

| | | | |
|---|---|---|---|
| 1,844,247 A | 2/1932 | Freemon | |
| 2,490,074 A | 12/1949 | Marty | |
| 2,699,771 A | 1/1955 | Ruttger-Pelli | |
| 5,336,159 A | 8/1994 | Cheng | |
| 6,056,204 A | 5/2000 | Glezer et al. | |
| 6,063,108 A * | 5/2000 | Salansky | A61N 5/0616 606/13 |

(Continued)

*Primary Examiner* — John R Downey
(74) *Attorney, Agent, or Firm* — Knobbe, Martens, Olson & Bear LLP (57) ABSTRACT

A phototherapy apparatus with interactive user interface for treating biological tissue of an animal or human target. The user interface comprises intuitive graphic menus which allow the clinicians or practitioners to define the properties of the biological tissue through easily observable physical characteristics such as weight, skin color, and hair color of the patient. The central control unit of the phototherapy apparatus then automatically optimizes the parameters of the light source according to the properties of the biological tissue and generates an appropriate treatment protocol to produce the optimum phototherapy result.

23 Claims, 5 Drawing Sheets

(56) References Cited

U.S. PATENT DOCUMENTS

| | | |
|---|---|---|
| 6,066,129 A | 5/2000 | Larson |
| 6,214,035 B1 | 4/2001 | Streeter |
| 6,413,268 B1 | 7/2002 | Hartman |
| 6,866,678 B2 | 3/2005 | Shenderova et al. |
| 7,033,382 B2 | 4/2006 | Lach |
| 7,083,580 B2 | 8/2006 | Bernabei |
| 7,144,247 B2 | 12/2006 | Black |
| 7,264,598 B2 | 9/2007 | Shin |
| 7,282,037 B2 | 10/2007 | Cho |
| 7,335,170 B2 | 2/2008 | Milne et al. |
| 7,749,178 B2 | 7/2010 | Imboden et al. |
| 7,762,964 B2 | 7/2010 | Slatkine |
| 9,216,300 B2 | 12/2015 | Pryor et al. |
| 9,498,640 B2 | 11/2016 | Pryor et al. |
| 9,764,155 B2 | 9/2017 | Pryor et al. |
| 10,086,211 B2 | 10/2018 | Pryor et al. |
| 2003/0163068 A1 | 8/2003 | Kang |
| 2003/0232303 A1 | 12/2003 | Black |
| 2004/0111133 A1 | 6/2004 | Huculak et al. |
| 2004/0138727 A1* | 7/2004 | Taboada ............... A61N 5/0622 607/88 |
| 2004/0193235 A1 | 9/2004 | Altshuler et al. |
| 2004/0193236 A1 | 9/2004 | Altshuler et al. |
| 2004/0236252 A1 | 11/2004 | Muzzi et al. |
| 2004/0260209 A1 | 12/2004 | Ella et al. |
| 2004/0260212 A1 | 12/2004 | Cho |
| 2005/0177140 A1 | 8/2005 | Jay |
| 2005/0177142 A1* | 8/2005 | Jay ......................... F04C 18/16 606/9 |
| 2006/0235494 A1 | 10/2006 | Vanderschuit |
| 2006/0253051 A1 | 11/2006 | Milne et al. |
| 2006/0259101 A1* | 11/2006 | Perez .................. A61N 5/0603 607/88 |
| 2007/0073366 A1 | 3/2007 | Porco |
| 2007/0096118 A1 | 5/2007 | Mahalingam et al. |
| 2007/0129776 A1 | 6/2007 | Robins et al. |
| 2008/0262394 A1 | 10/2008 | Pryor et al. |
| 2008/0262574 A1* | 10/2008 | Briefs .................. A61N 5/0616 607/88 |
| 2009/0001372 A1 | 1/2009 | Arik et al. |
| 2009/0012585 A1 | 1/2009 | Karni et al. |
| 2009/0234253 A1 | 9/2009 | Vandenbelt et al. |
| 2009/0299236 A1 | 12/2009 | Pryor et al. |
| 2011/0144725 A1 | 6/2011 | Pryor et al. |
| 2014/0296944 A1 | 10/2014 | Pryor et al. |
| 2016/0106889 A1 | 4/2016 | Pryor |
| 2017/0050042 A1 | 2/2017 | Pryor et al. |
| 2017/0128740 A1* | 5/2017 | Stephens ............. A61N 5/0616 |
| 2018/0093103 A1 | 4/2018 | Pryor et al. |

* cited by examiner

Choose Animal You Wish To Treat

PHOTOTHERAPY APPARATUS WITH INTERACTIVE USER INTERFACE

REFERENCE TO RELATED APPLICATION

This application claims an invention which was disclosed in Provisional Patent Application No. 61/285,762, filed Dec. 11, 2009, entitled "PHOTOTHERAPY APPARATUS WITH INTERACTIVE USER INTERFACE". The benefit under 35 USC § 119(e) of the above mentioned United States Provisional Applications is hereby claimed, and the aforementioned application is hereby incorporated herein by reference.

FIELD OF THE INVENTION

This invention generally relates to a phototherapy apparatus, and more specifically to a phototherapy apparatus with interactive user interface.

BACKGROUND

Phototherapy is a medical and veterinary technique which uses lasers, LEDs (light emitting diodes), or other types of light sources to stimulate or inhibit cellular function. Recently, this technique has been widely used for treating soft tissue injury, chronic pain, and promoting wound healing for both human and animal targets. The effectiveness of phototherapy is affected by a plurality of factors determined by the properties of the light source, e.g. wavelength, power density, energy fluence (dose), pulsing parameters (peak power, repetition rate, duty cycle), as well as by the physical characteristics of the patients, e.g. body-build, weight, gender, skin color, hair color, and body part to be treated, which in turn affects the absorption/scattering coefficient and penetration depth of the therapeutic light in the biological tissue. As a result, comprehensive training and knowledge about photon-tissue interaction are required for the clinicians or practitioners to obtain the optimum phototherapy result.

Existing phototherapy apparatus either require the clinicians or practitioners to control the above mentioned parameters of the light source directly or offer no control of these parameters at all. The former approach proves to be a formidable task for the clinicians or practitioners since they generally lack the knowledge about photon-tissue interaction. The latter approach does not yield the optimum phototherapy result or even produces adverse effects when improper light source parameters are applied.

There thus exists a need for an improved phototherapy apparatus which controls the parameters of the light source in accordance to the properties of the biological tissue so as to obtain the optimum phototherapy result and in the meantime does not require the clinicians or practitioners to possess comprehensive knowledge about photon-tissue interaction.

SUMMARY OF THE INVENTION

It is the overall goal of the present invention to solve the above mentioned problems and provide a phototherapy apparatus with an interactive user interface. The user interface comprises intuitive graphic menus which allow the clinicians or practitioners to define the properties of the biological tissue to be treated. The central control unit of the phototherapy apparatus then automatically optimizes the parameters of the light source according to the properties of the biological tissue and generates an appropriate treatment protocol to produce the optimum phototherapy result.

According to one aspect of the present invention, the user interface comprises intuitive drop-down and pop-up menus allowing the user to define the properties of the biological tissue through easily observable physical characteristics such as weight, skin color, and hair color of the patient.

According to another aspect of the present invention, the user interface comprises integrated 2-D and 3-D graphics and animations for both interacting and educating purposes.

According to yet another aspect of the present invention, the phototherapy apparatus can communicate with a remote server though a wireless or wired communication network for performing update on treatment protocols, manuals, educational illustrations and videos, etc. or for performing additional functions such as on-line billing, track of patient record, remote diagnosis of the patient, real-time monitoring of the phototherapy unit, etc.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to a phototherapy apparatus with interactive user interface. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 1:
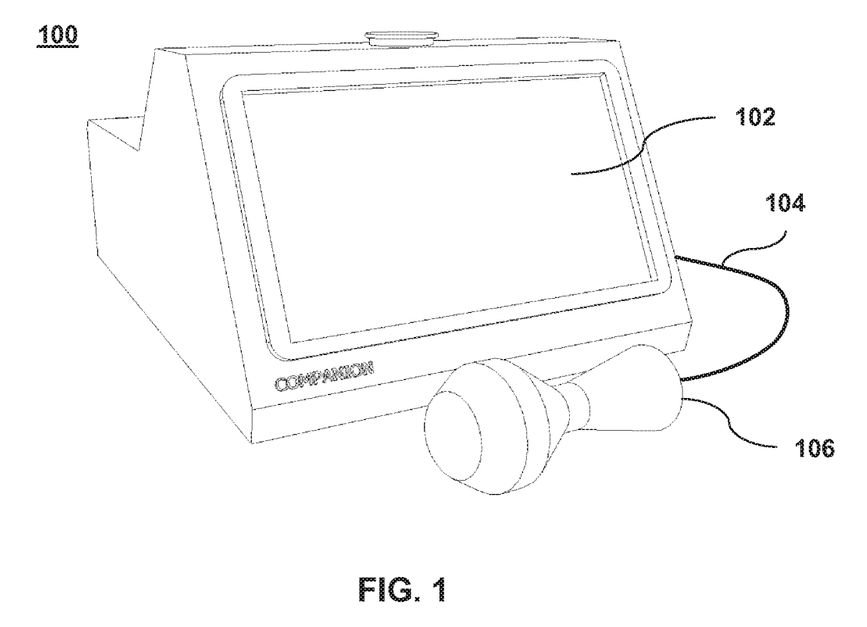
FIG. 1 shows an exemplary veterinary phototherapy apparatus with an interactive user interface.

FIG. 1 shows an exemplary veterinary phototherapy apparatus 100, which has a touch screen based interactive user interface 102. The light source (not shown) of the phototherapy apparatus 100 comprises three diode lasers operating at different wavelengths, e.g. 630 nm, 810 nm, and 980 nm. The output of the three lasers are combined and delivered via an optical fiber 104 to a hand piece 106, which controls the power density of the laser light and outputs the laser light to the subject biological tissue. The 630 nm visible laser has a low output power of <5 mW and is mainly used for aiming purposes. The two infrared lasers have high output power adjustable in the range of 1-10 W for producing photochemical reaction in the biological tissue, e.g. up-regulation and down-regulation of adenosine triphosphate (ATP), reactive oxygen species, and nitric oxide. The photochemical reaction in turn produces the following therapeutic effects: (i) stimulating white blood cell activity; (ii) accelerating macrophage activity, growth factor secretion and collagen synthesis; (iii) promoting revascularization and micro-circulation; (iv) increasing fibroblast numbers and collagen production; (v) accelerating epithelial cell regeneration and speeding up wound healing; (vi) increasing growth-phase-specific DNA synthesis; (vii) stimulating higher activity in cell proliferation and differentiation; (viii) increasing the intra and inter-molecular hydrogen bonding. The output wavelengths of the two infrared lasers are designed to treat biological tissues with different types and concentrations of chromophores. The 810 nm wavelength is well absorbed by the hemoglobin and melanin content of the biological tissue, while the 980 nm wavelength is efficiently absorbed by the water content. The output of the two infrared lasers can be combined at adjustable proportions and simultaneously applied to the biological tissue to achieve an enhanced treatment result. Both of the two infrared lasers can operate in a pulsed mode such that a high peak power is produced to increase the penetration depth of the laser light and/or to trigger nonlinear photochemical reactions yet the average power of the laser light is maintained at low levels to avoid any tissue damage.

Figure 2:
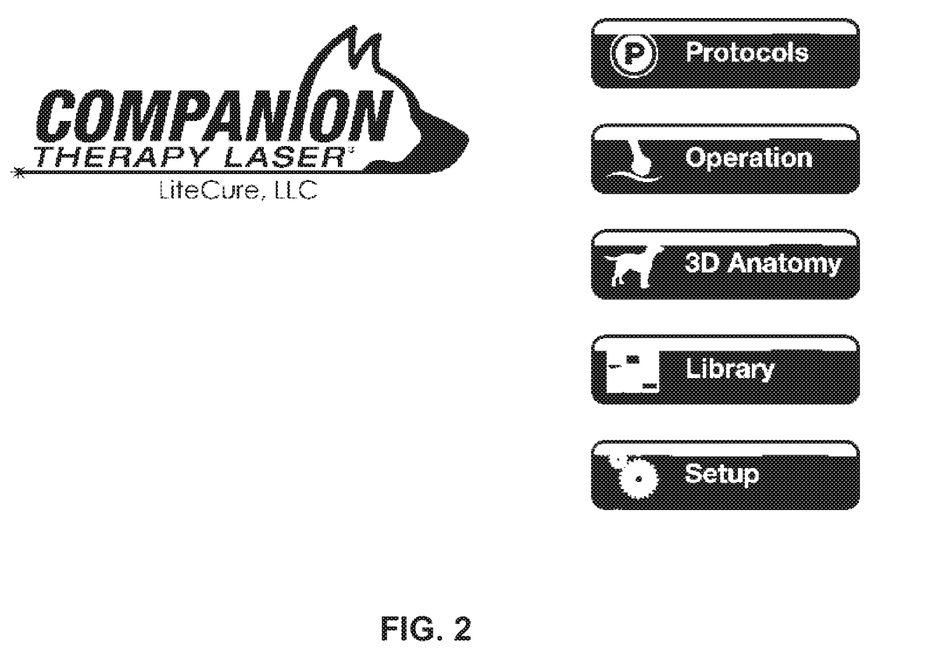
FIG. 2 shows the main menu of the interactive user interface of the veterinary phototherapy apparatus.

Referring to FIG. 2, the main menu of the interactive user interface 102 comprises several sub-menus which utilize 2-D and 3-D graphics and animations for assisting the clinicians or practitioners to optimize the treatment protocol of phototherapy. The 'Protocol' sub-menu allows the user to define the species, body weight, skin color, and hair color of the animal. The '3D Anatomy' sub-menu is used to define the medical condition and body part of the animal to be treated. Once the physical characteristics and medical conditions of the subject are properly defined, the central control unit (not shown) of the phototherapy apparatus 100 will generate an appropriate treatment protocol accordingly in the 'Operation' sub-menu such that the user can review and initiate the phototherapy process. For advanced users, the 'Operation' sub-menu also allows them to create self-defined treatment protocols by manually controlling the parameters of the light source. The main menu of the user interface also comprises a 'Library' sub-menu which provides introduction and education materials (such as treatment manuals, illustrations, and videos) related to phototherapy as well as a 'Setup' sub-menu for controlling the accessories of the phototherapy apparatus 100, e.g. aiming beam status, audio tone, foot-switch/hand-switch status, etc.

Figure 3:
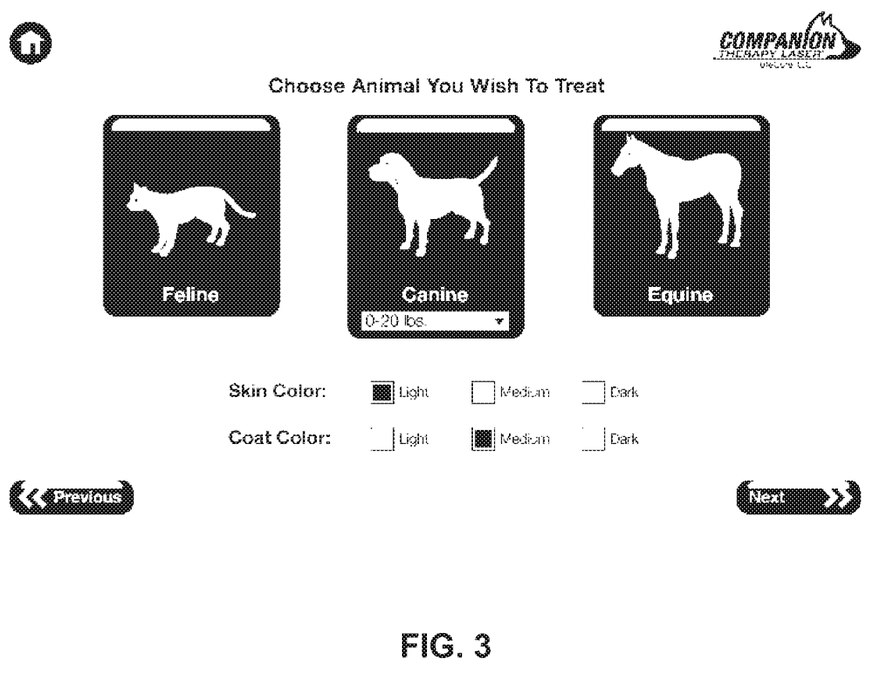
FIG. 3 shows a drop-down menu of the interactive user interface of FIG. 2 for defining the species, body weight, skin color, and hair color of the animal to be treated.

FIG. 3 shows the 'Protocol' sub-menu of the interactive user interface, which contains intuitive 2-D graphics for assisting the users to define the species, body weight, skin color, and hair color of the animal. Here the species and body weight (or the body-build) of the animal affects its skin thickness, skin density, as well as muscle and lipid content of the body, which in turn affects the absorption/scattering coefficient and penetration depth of the therapeutic light. The hair color of the animal, which is mainly determined by the content of two types of melanin, i.e. eumelanin and pheomelanin, determines the percentage loss of the therapeutic light in the coat of the animal. For animals with darker hair colors, it is desirable to use longer wavelengths, such as the 980 nm therapeutic light in this example, to avoid excessive power loss. The skin color of the animal reflects the type and content of chromophores (e.g. hemoglobin, melanin) existing in the skin tissue, which affects the absorption spectrum of the skin tissue as well as the penetration depth of the therapeutic light. A color palette (not shown) may be used here to define the skin and hair color even more precisely.

Figure 4:
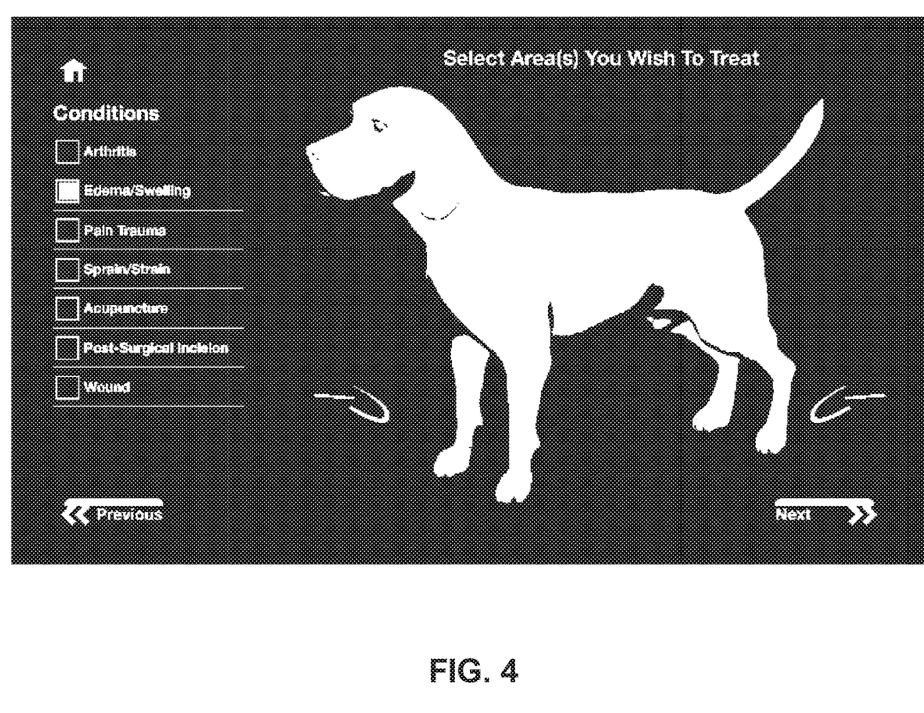
FIG. 4 shows another drop-down menu of the interactive user interface of FIG. 2 for defining the medical condition and body part of the animal to be treated.

FIG. 4 shows the '3D Anatomy' sub-menu of the interactive user interface, which contains a 3-D animation of the selected animal target for assisting the user to define the medical condition (e.g. arthritis, edema/swelling, pain trauma, sprain/strain, wound, and post-surgical incision) and body part of the animal to be treated. These two parameters are the main factors that determine the required wavelength, power density, energy fluence (dose), and pulsing parameters for the therapeutic light. For example, the medical condition of the animal determines which kind of photochemical reaction should be triggered in the tissue. Correspondingly, the laser wavelength, power density, energy fluence (dose), and pulsing parameters should be selected to produce the desired photochemical reaction most effectively. The medical condition also determines the required penetration depth for the therapeutic light. For example, the penetration depth can be small for edema/swelling treatment since only the skin tissue need to be treated. In this case, the laser wavelength shall be selected to match with the absorption band of the skin tissue, which can be estimated from the 'Protocol' sub-menu as disclosed above. Correspondingly, the power density and energy fluence of the laser light shall be kept at relatively low levels to avoid tissue damage. While for sprain/strain treatment, the penetration depth should be large enough to reach those inner muscle tissues. In this case, the laser wavelength shall be selected to match with the absorption band of the muscle tissue while deviating from those absorption bands of the skin tissue to avoid excessive power loss in the skin tissue. In the meantime, the power density and energy fluence of the laser light shall be relatively larger by considering the absorption/scattering loss of the laser light in the skin and coat of the animal. The laser parameters are also affected by the body parts to be treated. For limb treatment, the power density and penetration depth of the laser light can be small since the skin is relatively thin for these body parts. In comparison, higher power density and larger penetration depth are required to treat the trunk of the body.

Figure 5:
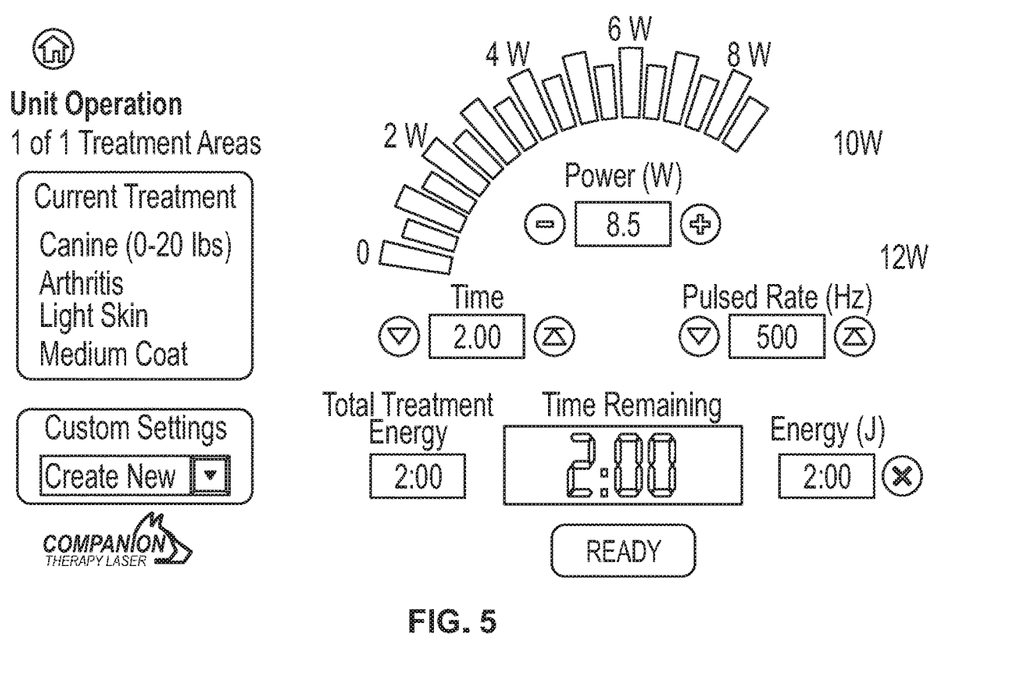
FIG. 5 shows an operation menu of the interactive user interface of FIG. 2 displaying an optimized treatment protocol.

Under the 'Protocol' sub-menu of FIG. 3 and the '3D Anatomy' sub-menu of FIG. 4, the properties of the subject biological tissue is defined by the user through those easily observable physical characteristics such as weight, skin color, hair color, and body part of the animal. In accordance to a summary of these properties and the medical condition to be treated, the central control unit of the phototherapy apparatus will automatically generate an appropriate treatment protocol, which controls the laser wavelength, power density, pulsing parameters, and duration time of the phototherapy procedure. FIG. 5 shows an exemplary treatment protocol displayed on the 'Operation' sub-menu of the interactive user interface. Here the laser wavelength (or the relative power ratio between different laser wavelengths if multiple lasers are used simultaneously) is determined by: (i) the medical condition to be treated (hence the photochemical reaction to be produced); (ii) the skin color of the animal, which affects the skin's absorption spectrum; and (iii) the hair color of the animal to avoid excessive laser power loss in the animal's coat. The required power density and energy fluence (dose) for the laser light is determined by: (i) the medical condition to be treated; (ii) the species and weight of the animal, which influences its skin thickness, skin density, as well as muscle and lipid content of the body, hence affecting the penetration depth of the laser light; (iii) the body part to be treated; and (iv) the skin color of the animal, which determines its absorption coefficient for the laser light. Similarly, the pulsing parameters of the laser are optimized according to: (i) the medical condition to be treated; (ii) the species and weight of the animal; (iii) the body part to be treated; and (iv) the skin color of the animal. It is worth to note that the laser parameters can be adjusted during the phototherapy procedure to achieve optimized treatment results. As an additional feature, the whole treatment protocol optimization process as disclosed above together with those 2-D and 3-D graphics and animations may serve as an educational tool for training the clinicians or practitioners in phototherapy technology.

In the above disclosed procedure, the treatment protocol is optimized primarily based on the medical condition to be treated with certain adjustments of laser parameters based on the physical characteristics of the animal. For each medical condition, the optimum treatment protocol can be obtained from previous studies and clinical trials and stored in a database in the central control unit. Based on the user entered physical characteristics of the animal, the central control unit can estimate the absorption and scattering coefficient of the tissue and the penetration depth of the laser light so as to adjust the laser parameters accordingly to generate an optimum treatment protocol for the specific animal target. This optimization process can be automatically completed by the central control unit. Thus the clinician or practitioner does not need to possess any comprehensive knowledge about photon-tissue interaction. This feature allows the phototherapy apparatus to be used even by amateur users such as pet owners for 'take-home' treatment. The central control unit can track the usage of the phototherapy apparatus for medical record and billing purposes. For advanced users, the 'Operation' sub-menu also allows them to manually control the laser parameters to create their own treatment protocols. In a slight variation of the present embodiment, certain laser parameters (e.g. laser wavelength, power density, energy fluence, pulsing parameters) can be hidden away from the 'Operation' sub-menu as a protection of proprietary treatment protocols.

In another exemplary embodiment of the present invention, the interactive user interface further comprises a 'Communication' sub-menu for communicating with a remote server though a wireless or wired communication network. The 'Communication' sub-menu can be used for performing update on treatment protocols, manuals, educational illustrations and videos, etc. or for performing additional functions such as on-line billing, track of patient record, remote diagnosis of the patient, real-time monitoring of the phototherapy unit, etc.

In the foregoing specification, specific embodiments of the present invention have been described. However, one of ordinary skill in the art appreciates that various modifications and changes can be made without departing from the scope of the present invention as set forth in the claims below. The numerical values cited in the specific embodiment are illustrative rather than limiting. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A method comprising:
   presenting, by a touchscreen of a phototherapy apparatus, a concurrent display of multiple first selectable interface elements that are associated with different animal species, including:
   (i) a selectable interface element that graphically depicts a first animal species,
   (ii) a selectable interface element that graphically depicts a second animal species, and
   (iii) a selectable interface element that graphically depicts a third animal species;
   receiving, by the phototherapy apparatus and through physical interaction with the touchscreen, user selection of one of the multiple first selectable interface elements that is associated with a selected animal species of the different animal species;
   presenting, by the touchscreen of the phototherapy apparatus, a concurrent display of multiple second selectable interface elements that are associated with different animal colors;
   receiving, by the phototherapy apparatus and through physical interaction with the touchscreen, user selection of one of the multiple second selectable interface elements that is associated with a selected animal color of the different animal colors;
   presenting, by the touchscreen of the phototherapy apparatus, a concurrent display of multiple third selectable interface elements that are associated with different animal conditions;
   receiving, by the phototherapy apparatus and through physical interaction with the touchscreen, user selection of one of the multiple third selectable interface elements that is associated with a selected animal condition of the different animal conditions;
   selecting, by the phototherapy apparatus, parameters of light for administration by a hand piece of the phototherapy apparatus that is operatively connected to a main body of the phototherapy apparatus, in accordance with (a) the user selection of the one of the multiple first selectable interface elements that is associated with the selected animal species, (b) the user selection of the one of the multiple second selectable interface elements that is associated with the selected animal color, and (c) the user selection of the one of the multiple third selectable interface elements that is associated with the selected animal condition; and presenting, by the touchscreen of the phototherapy apparatus in response to the phototherapy apparatus having selected the parameters of light for administration by the hand piece of the phototherapy apparatus, a concurrent display in a treatment screen of:
  (i) an indication of a time of treatment, and
  (ii) an indication of a power of treatment.

2. The method of claim 1, wherein:
the graphical depiction of the first animal species is a graphical depiction of a feline;
the graphical depiction of the second animal species is a graphical depiction of a canine, and
the graphical depiction of the third animal species is a graphical depiction of an equine.

3. The method of claim 1, wherein:
the graphical depiction of the first animal species is a graphical depiction of the first animal species within a first box, accompanied by text within the first box that identifies the first animal species,
the graphical depiction of the second animal species is a graphical depiction of the second animal species within a second box, accompanied by text within the second box that identifies the second animal species, and
the graphical depiction of the third animal species is a graphical depiction of the third animal species within a third box, accompanied by text within the third box that identifies the third animal species.

4. The method of claim 1, wherein the concurrent display of the multiple second selectable interface elements that are associated with the different animal colors includes:
  (i) a selectable interface element associated with light animal color; and
  (ii) a selectable interface element associated with dark animal color.

5. The method of claim 1, wherein the concurrent display of the multiple second selectable interface elements that are associated with the different animal colors includes:
  (i) a user selectable box accompanied by text that that identifies "light" animal color; and
  (ii) a user selectable box accompanied by text that identifies "dark" animal color.

6. The method of claim 5, wherein the concurrent display of the multiple second selectable interface elements is presented concurrently with:
  (i) a home interface element that graphically depicts a house; and
  (ii) a previous screen interface element that graphically depicts a leftward-facing arrow.

7. The method of claim 1, wherein the concurrent display of the multiple third selectable interface elements that are associated with the different animal conditions includes multiple respective user-selectable boxes associated with the different animal conditions, accompanied by corresponding text that identifies the different animal conditions.

8. The method of claim 7, wherein the different animal conditions include an edema/swelling condition.

9. The method of claim 1, wherein the concurrent display of the multiple third selectable interface elements is presented concurrently with a graphical depiction of the selected animal species.

10. The method of claim 1, wherein the concurrent display in the treatment screen includes:
  (iii) a frequency of light administered by the hand piece of the phototherapy apparatus; and
  (iv) an energy of treatment.

11. The method of claim 1, wherein the indication of the time of treatment concurrently displayed in the treatment screen with the indication of the power of treatment includes (a) an indication of total time of treatment, and (b) an indication of time remaining of treatment.

12. A phototherapy apparatus, comprising:
a light source to produce light;
a central control unit that is configured to automatically select parameters of light for administration by the light source, in accordance with user selections; and
a touchscreen that is configured with the central control unit, through presentation of interface elements that are to be indicated by the central control unit, to allow user selections to define medical conditions and physical characteristics of an animal target by operations that include:
  presenting, by the touchscreen of the phototherapy apparatus, a concurrent display of multiple first selectable interface elements that are associated with different animal species, including:
    (i) a selectable interface element that graphically depicts a first animal species,
    (ii) a selectable interface element that graphically depicts a second animal species, and
    (iii) a selectable interface element that graphically depicts a third animal species;
  receiving, by the phototherapy apparatus and through physical interaction with the touchscreen, user selection of one of the multiple first selectable interface elements that is associated with a selected animal species of the different animal species;
  presenting, by the touchscreen of the phototherapy apparatus, a concurrent display of multiple second selectable interface elements that are associated with different animal colors;
  receiving, by the phototherapy apparatus and through physical interaction with the touchscreen, user selection of one of the multiple second selectable interface elements that is associated with a selected animal color of the different animal colors;
  presenting, by the touchscreen of the phototherapy apparatus, a concurrent display of multiple third selectable interface elements that are associated with different animal conditions;
  receiving, by the phototherapy apparatus and through physical interaction with the touchscreen, user selection of one of the multiple third selectable interface elements that is associated with a selected animal condition of the different animal conditions; and
  presenting, by the touchscreen of the phototherapy apparatus in response to the central control unit having selected the parameters of light for administration by the hand piece of the phototherapy apparatus in accordance with (a) the user selection of the one of the multiple first selectable interface elements that is associated with the selected animal species, (b) the user selection of the one of the multiple second selectable interface elements that is associated with the selected animal color, and (c) the user selection of the one of the multiple third selectable interface elements that is associated with the selected animal condition, a concurrent display in a treatment screen of:
    (i) an indication of a time of treatment, and
    (ii) an indication of a power of treatment.

13. The phototherapy apparatus of claim 12, wherein:
the graphical depiction of the first animal species is a graphical depiction of a feline;
the graphical depiction of the second animal species is a graphical depiction of a canine, and
the graphical depiction of the third animal species is a graphical depiction of an equine.

14. The phototherapy apparatus of claim 12, wherein:
the graphical depiction of the first animal species is a graphical depiction of the first animal species within a first box, accompanied by text within the first box that identifies the first animal species,
the graphical depiction of the second animal species is a graphical depiction of the second animal species within a second box, accompanied by text within the second box that identifies the second animal species, and
the graphical depiction of the third animal species is a graphical depiction of the third animal species within a third box, accompanied by text within the third box that identifies the third animal species.

15. The phototherapy apparatus of claim 12, wherein the concurrent display of the multiple second selectable interface elements that are associated with the different animal colors includes:
(i) a selectable interface element associated with light animal color; and
(ii) a selectable interface element associated with dark animal color.

16. The phototherapy apparatus of claim 12, wherein the concurrent display of the multiple second selectable interface elements that are associated with the different animal colors includes;
(i) a user selectable box accompanied by text that that identifies "light" animal color; and
(ii) a user selectable box accompanied by text that identifies "dark" animal color.

17. The phototherapy apparatus of claim 16, wherein the concurrent display of the multiple second selectable interface elements is presented concurrently with:
(i) a home interface element that graphically depicts a house; and
(ii) a previous screen interface element that graphically depicts a leftward-facing arrow.

18. The phototherapy apparatus of claim 12, wherein the concurrent display of the multiple third selectable interface elements that are associated with the different animal conditions includes multiple respective user-selectable boxes associated with the different animal conditions, accompanied by corresponding text that identifies the different animal conditions.

19. The phototherapy apparatus of claim 12, wherein the concurrent display of the multiple third selectable interface elements is presented concurrently with a graphical depiction of the selected animal species.

20. The phototherapy apparatus of claim 12, wherein the concurrent display in the treatment screen includes:
(iii) a frequency of light administered by the hand piece of the phototherapy apparatus; and
(iv) an energy of treatment.

21. The phototherapy apparatus of claim 12, wherein the indication of the time of treatment concurrently displayed in the treatment screen with the indication of the power of treatment includes (a) an indication of total time of treatment, and (b) an indication of time remaining of treatment.

22. A method comprising:
presenting, by a touchscreen of a phototherapy apparatus, a concurrent display of multiple first selectable interface elements that are associated with different animal species, including:
(i) a selectable interface element that graphically depicts a feline within a first box, accompanied by text within the first box that identifies the feline,
(ii) a selectable interface element that graphically depicts a canine within a second box, accompanied by text within the second box that identifies the canine, and
(iii) a selectable interface element that graphically depicts an equine within a third box, accompanied by text within the third box that identifies the equine;
receiving, by the phototherapy apparatus and through physical interaction with the touchscreen, user selection of one of the multiple first selectable interface elements that is associated with a selected animal species of the different animal species;
presenting, by the touchscreen of the phototherapy apparatus, a concurrent display of multiple second selectable interface elements that are associated with different animal colors, including:
(i) a user selectable box accompanied by text that that identifies light animal color, and
(ii) a user selectable box accompanied by text that identifies dark animal color;
receiving, by the phototherapy apparatus and through physical interaction with the touchscreen, user selection of one of the multiple second selectable interface elements that is associated with a selected animal color of the different animal colors;
presenting, by the touchscreen of the phototherapy apparatus, a concurrent display of multiple third selectable interface elements that are associated with different animal conditions, presented concurrently with a graphical depiction of the selected animal species;
receiving, by the phototherapy apparatus and through physical interaction with the touchscreen, user selection of one of the multiple third selectable interface elements that is associated with a selected animal condition of the different animal conditions;
selecting, by the phototherapy apparatus, parameters of light for administration by a hand piece of the phototherapy apparatus that is operatively connected to a main body of the phototherapy apparatus, in accordance with (a) the user selection of the one of the multiple first selectable interface elements that is associated with the selected animal species, (b) the user selection of the one of the multiple second selectable interface elements that is associated with the selected animal color, and (c) the user selection of the one of the multiple third selectable interface elements that is associated with the selected animal condition; and
presenting, by the touchscreen of the phototherapy apparatus in response to the phototherapy apparatus having selected the parameters of light for administration by the hand piece of the phototherapy apparatus, a concurrent display in a treatment screen of:
(i) an indication of total time of treatment,
(ii) an indication of time remaining of treatment,
(iii) an indication of a power of treatment,
(iv) a frequency of light administered by the hand piece, and
(v) an energy of treatment.

23. A phototherapy apparatus, comprising:

a light source to produce light;

a central control unit that is configured to automatically select parameters of light for administration by the light source, in accordance with user selections; and a touchscreen that is configured with the central control unit, through presentation of interface elements that are to be indicated by the central control unit, to allow user selections to define medical conditions and physical characteristics of an animal target by operations that include:

presenting, by the touchscreen of the phototherapy apparatus, a concurrent display of multiple first selectable interface elements that are associated with different animal species, including:

(i) a selectable interface element that graphically depicts a feline within a first box, accompanied by text within the first box that identifies the feline, (ii) a selectable interface element that graphically depicts a canine within a second box, accompanied by text within the second box that identifies the canine, and (iii) a selectable interface element that graphically depicts an equine within a third box, accompanied by text within the third box that identifies the equine;

receiving, by the phototherapy apparatus and through physical interaction with the touchscreen, user selection of one of the multiple first selectable interface elements that is associated with a selected animal species of the different animal species;

presenting, by the touchscreen of the phototherapy apparatus, a concurrent display of multiple second selectable interface elements that are associated with different animal colors, including:

(i) a user selectable box accompanied by text that that identifies light animal color, and (ii) a user selectable box accompanied by text that identifies dark animal color;

receiving, by the phototherapy apparatus and through physical interaction with the touchscreen, user selection of one of the multiple second selectable interface elements that is associated with a selected animal color of the different animal colors;

presenting, by the touchscreen of the phototherapy apparatus, a concurrent display of multiple third selectable interface elements that are associated with different animal conditions, presented concurrently with a graphical depiction of the selected animal species;

receiving, by the phototherapy apparatus and through physical interaction with the touchscreen, user selection of one of the multiple third selectable interface elements that is associated with a selected animal condition of the different animal conditions;

selecting, by the phototherapy apparatus, parameters of light for administration by a hand piece of the phototherapy apparatus that is operatively connected to a main body of the phototherapy apparatus, in accordance with (a) the user selection of the one of the multiple first selectable interface elements that is associated with the selected animal species, (b) the user selection of the one of the multiple second selectable interface elements that is associated with the selected animal color, and (c) the user selection of the one of the multiple third selectable interface elements that is associated with the selected animal condition; and presenting, by the touchscreen of the phototherapy apparatus in response to the central control unit having selected the parameters of light for administration by the hand piece of the phototherapy apparatus in accordance with (a) the user selection of the one of the multiple first selectable interface elements that is associated with the selected animal species, (b) the user selection of the one of the multiple second selectable interface elements that is associated with the selected animal color, and (c) the user selection of the one of the multiple third selectable interface elements that is associated with the selected animal condition, a concurrent display in a treatment screen of:

(i) an indication of total time of treatment, (ii) an indication of time remaining of treatment, (iii) an indication of a power of treatment, (iv) a frequency of light administered by the hand piece, and (v) an energy of treatment.

* * * * *